US007081087B2

(12) United States Patent
Jannuzzi

(10) Patent No.: US 7,081,087 B2
(45) Date of Patent: Jul. 25, 2006

(54) SEXUAL AID DEVICE

(76) Inventor: Carmella Jannuzzi, 14 Montgomery Ave., Staten Island, NY (US) 10301

( * ) Notice: Subject to any disclaimer, the term of this patent is extended or adjusted under 35 U.S.C. 154(b) by 0 days.

(21) Appl. No.: 10/772,558

(22) Filed: Feb. 5, 2004

(65) Prior Publication Data

US 2004/0186344 A1 Sep. 23, 2004

Related U.S. Application Data

(60) Provisional application No. 60/445,212, filed on Feb. 5, 2003.

(51) Int. Cl.
*A61F 5/00* (2006.01)

(52) U.S. Cl. ........................................................ 600/38

(58) Field of Classification Search ............ 600/38–41; D24/314, 315; 601/46, 67, 69–74, 78–81, 601/47

See application file for complete search history.

(56) References Cited

U.S. PATENT DOCUMENTS 2,957,474 A * 10/1960 Bates et al. ................. 601/135
3,504,665 A * 4/1970 Bakunin et al. .............. 601/71
4,002,164 A * 1/1977 Bradley ...................... 601/135
4,917,104 A * 4/1990 Rebell ........................ 600/585
5,690,603 A * 11/1997 Kain ........................... 600/38
5,853,362 A * 12/1998 Jacobs ......................... 600/38
6,132,366 A * 10/2000 Ritchie et al. ................ 600/38
6,190,307 B1 * 2/2001 Tsai ............................ 600/38
6,758,826 B1 * 7/2004 Luettgen et al. .............. 601/73

OTHER PUBLICATIONS

Webster's Ninth New Collegiate Dictionary, p. 1313, vibrate.*

* cited by examiner

*Primary Examiner*—Samuel G. Gilbert
(74) *Attorney, Agent, or Firm*—Wolf Block Schorr & Solis-Cohen LLP

(57) ABSTRACT

A sexual aid device comprising a curved portion having a proximal and a distal end, a substantially straight portion, the straight portion extending from the proximal end of the curved portion thereby forming an approximate J shape, and a rod and an electric motor for causing movement of the curved portion is provided. The movement can be arcuate, circular, vibratory, an extending movement or a "come hither" back-and-forth movement. The distal end of the curved portion stimulates a female's Grafenberg spot or G spot when the device is inserted into the vagina with the straight portion pointing away from the curved portion towards the female's torso. The straight portion extends coextensively from the curved portion. The device also includes a clitoral stimulation portion which is textured and vibrates.

13 Claims, 3 Drawing Sheets

SEXUAL AID DEVICE

RELATED APPLICATIONS

This application claims the benefit of U.S. Provisional Application No. 60/445,212, filed Feb. 5, 2003.

FIELD OF THE INVENTION

The present invention relates to articles adapted to enhance sexual functioning and to provide sexual stimulation, and in particular, to such devices adapted to be inserted into the vagina.

BACKGROUND OF THE INVENTION

Numerous devices are commercially available which are adapted to enhance sexual function and to provide sexual stimulation. The majority of the devices that are commercially available may be generally described as either a dildo, i.e. a non-vibratory article adapted for either anal or vaginal insertion, or a vibrator, i.e. an article including means for generating a vibration to enhance sexual stimulation. Although dildos and vibrators come in wide array of designs and styles they tend to be generally elongated and cylindrical in shape since this shape is best anatomically suited for vaginal and/or anal insertion.

Many known dildos and vibrators are substantially straight from one end of the device to the other. When a straight dildo or vibrator is used for self-stimulation, it is often somewhat difficult to initially insert the device into the selected body cavity. Specifically, insertion into either the vagina or anus requires considerable bending at the waist, or in the alternative, requires the individual to perform a deep squat maneuver to achieve penetration. Further, once penetration is achieved, it is difficult to reach the exposed portion of the device for manual manipulation purposes. Thus, manual manipulation of the device once it is inserted into the selected body cavity also requires significant manipulation at the waist. Accordingly, it is not possible to comfortably utilize the device in the fully supine position.

Some known dildos and vibrators are specifically shaped to target specific areas within the body cavity, such as the paraurethral gland of the urethral sponge in women (also called the Grafenberg spot or G spot) or the prostate gland in men. These devices, i.e. those devices adapted to target a specific area within the body cavity, are usually provided with a slight curvature that enables the device to be more easily delivered to, and positioned at, the target area. Although, once inserted, curved dildos and vibrators are effective at reaching and stimulating a targeted area they have many of the same problems as straight dildos or vibrators during initial insertion into the body cavity. That is, in order to insert a curved dildo or vibrator into the selected body cavity significant bending at the waist is required, or in the alternative, a deep squat type of maneuver must be performed. Likewise, once the curved dildo or vibrator is inserted, significant bending at the waist is required in order to manually manipulate the device. Thus, again, the device cannot be easily manually self-manipulated when in the fully supine position.

Although, as mentioned above, dildos and vibrators come in a wide array of sizes and styles, known devices tend to be rather compact in nature for a number of reasons. First, the overall size of the device, including the length and girth of the device, is limited by anatomical considerations. That is, only a relatively short length of the device may be received within either the vagina or the anus. Further, known devices are generally compact in nature for portability considerations, i.e. so that the device may be easily carried and conveniently stored in a small bag or the like: Finally, known devices are relatively compact for privacy purposes, that is, so that the device can be easily stored in a private and secure location when the device is not in use.

Since known devices are generally rather compact in nature, as discussed above, once the device is inserted within the vagina or anus, only a relatively small portion of the device is externally accessible to the user. As such, when in the supine position, it is difficult to reach the externally accessible portion of the device. Often, when in the fully supine position, it is difficult to reach the externally accessible portion of the device whatsoever. As a result of the foregoing, if manual self-manipulation of the device is desired, the user must bend at the waist to reach the device, which is inconvenient and uncomfortable.

OBJECTS AND SUMMARY OF THE INVENTION

It is therefore an object of the present invention to provide an improved sexual aid device that overcomes the disadvantages of the prior art devices described above.

It is further an object of the present invention to provide an improved sexual aid device that can be easily inserted into a selected body cavity and manually self-manipulated when in supine position.

In view of the foregoing objectives, the sexual aid device according to the present invention includes a first curved portion and a second substantially straight elongated portion that extends coextensively from the curved portion. The curved portion and the substantially straight portion are structured and arranged such that when the curved portion is inserted within the vagina the straight portion extends in direction towards the user's torso. In this manner, a user may comfortably insert the distal tip of the device into her vagina while in the supine position. Moreover, once the distal tip is inserted within the vagina a user can easily grasp the substantially straight portion while in the supine position to thereby enable manual self-manipulation of the device.

DETAILED DESCRIPTION OF THE INVENTION

Figure 1:
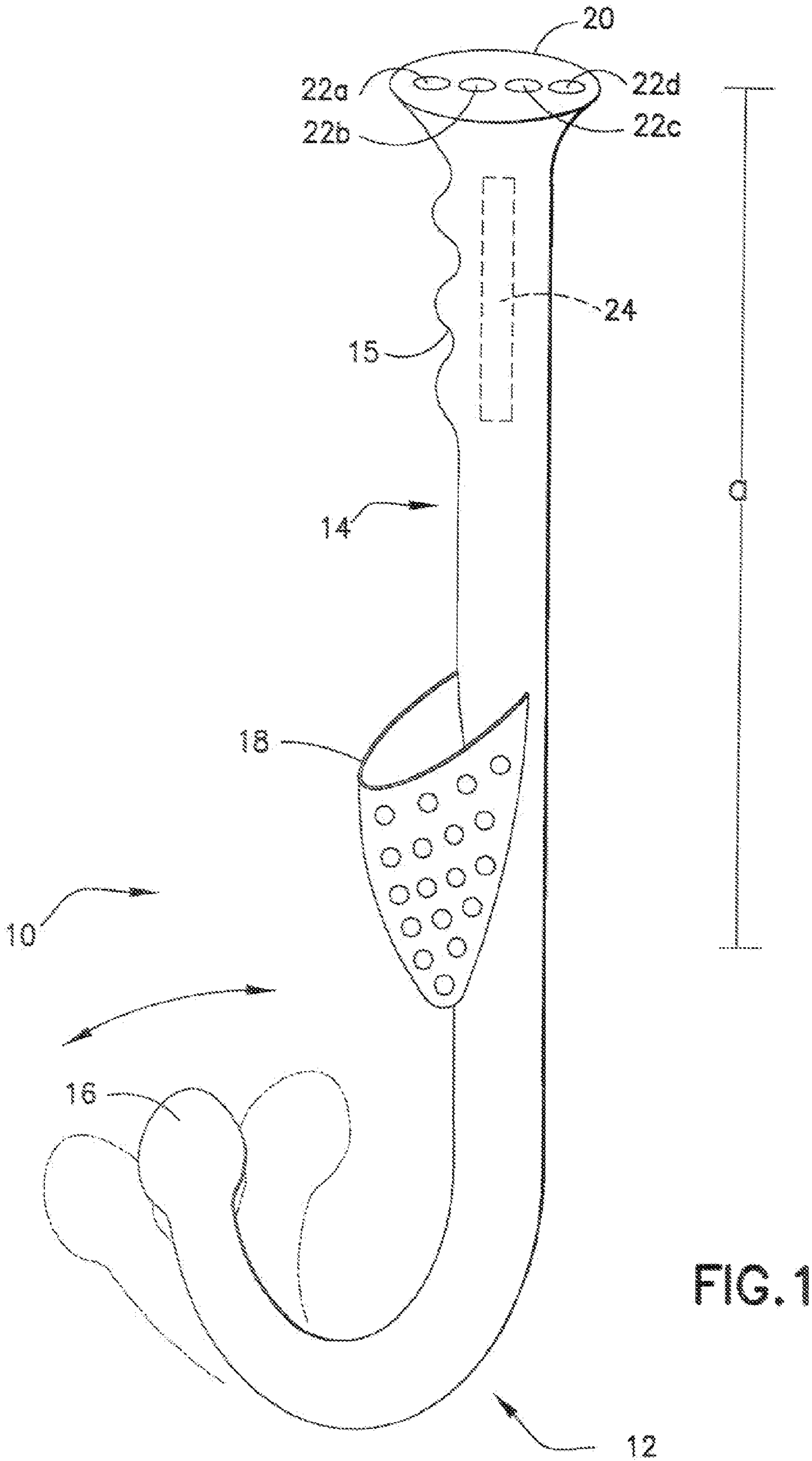
FIG. 1 is a perspective view of the sexual aid device according to the present invention.
Figure 2:
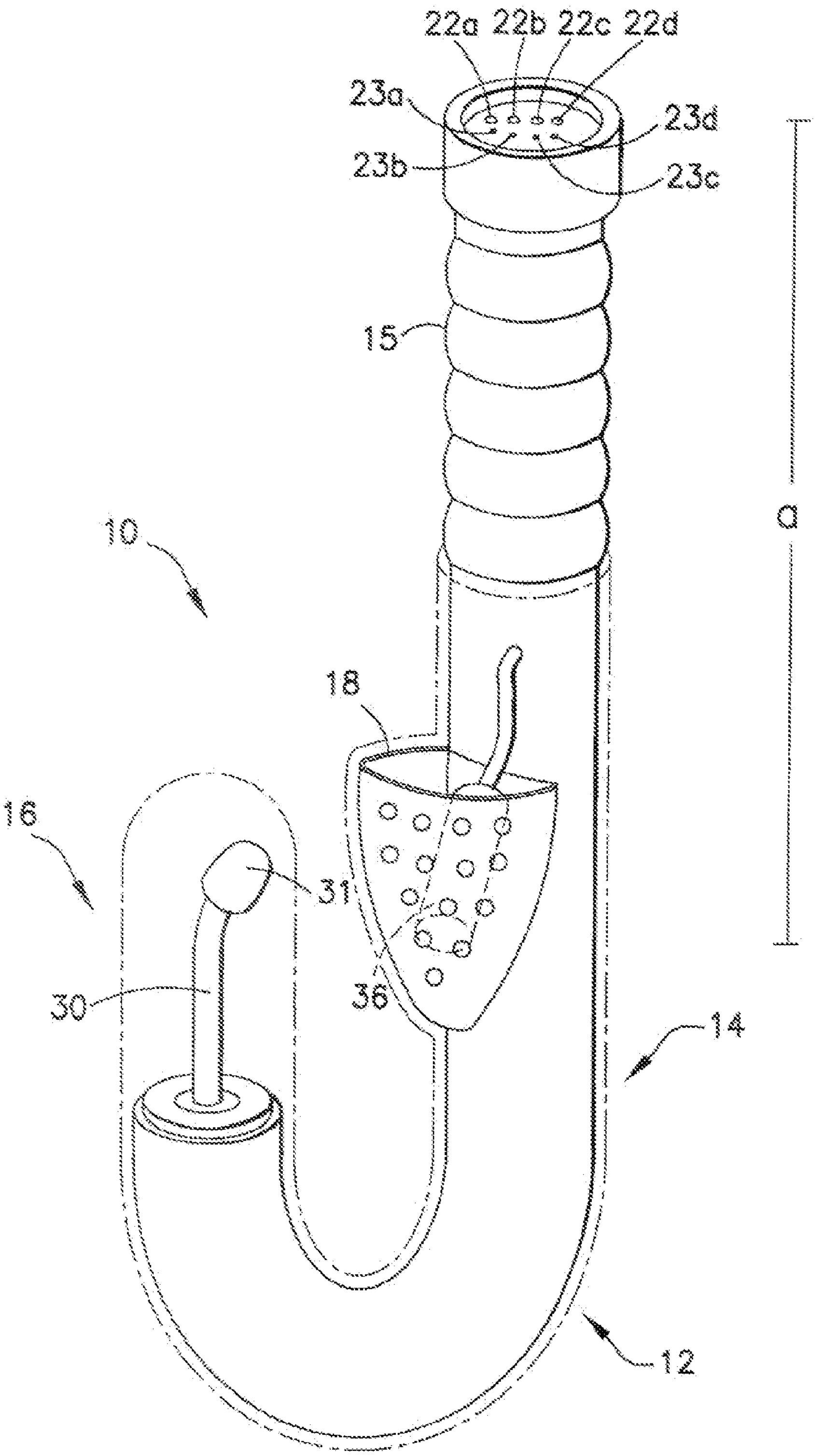
FIG. 2 is a partial cut-away view of the sexual aid device according to the present invention.
Figure 3:
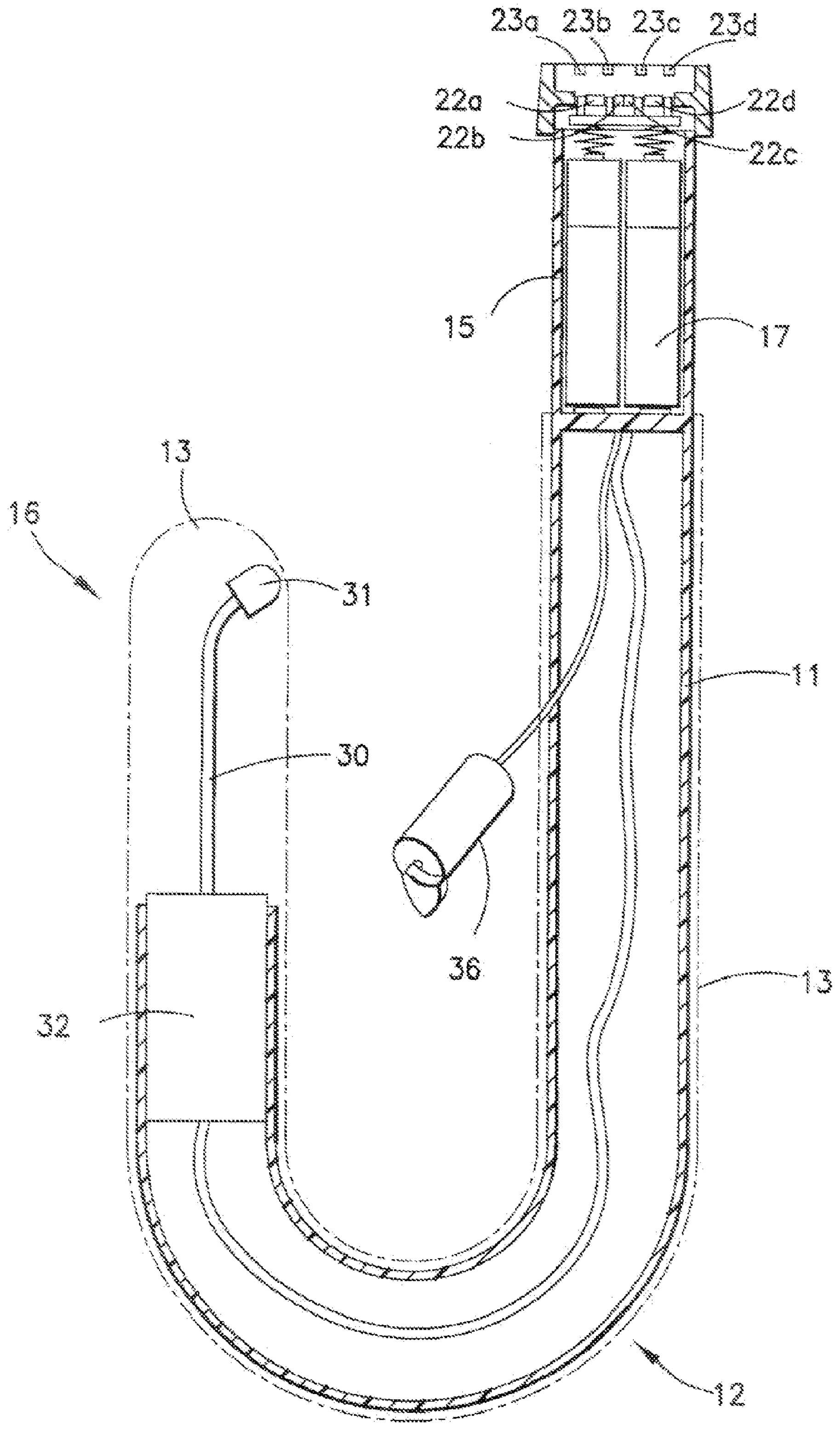
FIG. 3 is a cross-sectional view of the sexual aid device according to the present invention.

Referring to FIGS. 1–3, a sexual aid device according to the present invention is generally designated by the numeral 10. The device 10 comprises a large plastic housing 11 which may be made of 2 pieces. This plastic housing 11 is then sheathed in a silicon sleeve or overmold 13. As shown, the sexual aid device 10 includes a first curved portion 12 and a second substantially straight elongated portion 14 that extends coextensively from the curved portion 12 forming an approximate J shape. The curved portion 12 is adapted to be inserted within the vagina, although it may be inserted within the anus. Preferably, the distal tip 16 of the curved portion 12 is shaped like a male penis. However, of course, the distal tip 16 may be structured to have other shapes. The curved portion 12 and the substantially straight portion 14 are structured and arranged such that when the curved portion 12 is inserted within the vagina the straight portion extends in direction towards the user's torso. In this manner, a user may comfortably insert the distal tip 16 of the device into her vagina while in the supine position. Moreover, once the distal tip 16 is inserted within the vagina, a user can easily grasp the substantially straight portion 14 while in the supine position to thereby enable manual self-manipulation of the device.

To enable the substantially straight portion 14 to be easily grasped while in the supine position, the straight portion 14 preferably has a length "a" of approximately 10–12". In addition, as shown in the Figure, the substantially straight portion 14 may be provided with a hand grip 15 or the like at a proximal end thereof to aid the user in grasping and controlling the movement of the device. Located inside the plastic housing 11 are batteries 17. The curved portion 12 preferably has a length of approximately 4". Thus, the device 10 preferably has an overall length of approximately 14" to 16".

The device 10 is further provided with clitoral stimulation cup portion 18. The clitoral stimulation cup portion 18 is structured and arranged such that when the curved portion 12 is inserted within the vagina the cup portion 18 is placed in abutment with the clitoris to thereby provide stimulation of the same. The surface of the clitoral stimulation cup portion 18 is preferably provided with a textured surface, e.g. raised nipples, to thereby enhance clitoral stimulation.

The clitoral stimulation cup portion 18 is preferably mounted to the straight portion 14 such that its vertical position on the straight portion 14 may be selectively adjusted by the user. For example, the straight portion 14 could be provided with a slotted groove having a plurality of slots or the like and the clitoral stimulation cup portion 18 could be provided a post which extends from a rear surface of the clitoral stimulation cup portion 18, the post being structured and arranged to be inserted into one of the slots in the slotted groove. In this manner, the user could selectively position the clitoral stimulation cup portion 18 as desired.

The device 10 is preferably provided means to impart an arcuate movement to distal tip 16 as shown in FIG. 1. The means to impart the arcuate movement may comprise, for example, a wire or small flexible or rigid rod 30 that passes through the body of device, the rod 30 being operably coupled to an electric motor 32 for imparting an arcuate movement to the distal tip 31 of the rod 30. The electric motor 32 is wired to the batteries 17. The electric motor 32 may move at varying speeds. The distal tip 31 of the rod 30 being internally arranged near the distal tip 16 of the curved portion 12 such that when the distal tip 31 of the rod 30 moves in an arcuate fashion, the distal tip 16 of the curved portion 12 likewise moves in an arcuate manner as shown. The curved portion 12 is constructed from a suitable flexible material such as the silicone overmold 13 that permits the arcuate movement as described. The arcuate movement of the distal 16 is adapted to provide enhanced G-spot stimulation by tapping the G-spot. The movement may also be in a "back-and-forth" or a "come hither" direction. In addition, the movement may be in a circular or in an extending direction.

The device 10 is also preferably provided with means to impart a vibratory effect to the curved portion 12 of the device. Any conventional known means to impart such vibration effect may be used, for example an electrical coil that vibrates when a DC current is applied may be used to impart said vibratory effect. The DC motor 32 which moves rod 30 may provide a vibratory effect to the curved portion 12 of the device.

The device 10 is also preferably provided with means to impart a vibratory effect to the clitoral stimulation cup portion 18. Again, any know means may be utilized to impart the vibratory effect to the clitoral stimulation cup portion 18. For example, as described above a electrical coil that vibrates when a DC current is applied may be used to impart said vibratory effect. As shown in FIGS. 2–3, DC motor 36 located within the clitoral stimulation cup portion 18 provides the vibratory effect to the clitoral stimulation cup portion 18. The DC motor 36 is wired to the batteries 17.

The device 10 includes a cover 20 located at a proximal end of the device. The cover 20 is hingedly mounted to the device such that the cover may be selectively opened and closed to provide access to an internal chamber 24 within the device 10. The internal chamber is adapted to receive batteries that power the means for imparting the arcuate motion to the distal tip 16, the means for imparting the vibratory effect to the curved portion 12 and the means for imparting the vibratory effect to the clitoral stimulation cup portion 18.

The cover 20 is provided with four buttons or the like 22*a*, 22*b*, 22*c* and 22*d* and a plurality of LED's 23. Each of the buttons is operably connected to a switch or the like that is adapted to control the flow of electrical current from the batteries to the means for imparting the arcuate motion to the distal tip 16, the means for imparting the vibratory effect to the curved portion 12 and the means for imparting the vibratory effect to the clitoral stimulation cup portion 18. Button 22*a* is operably coupled to a switch that controls the flow of current to the means for imparting the vibratory effect to the curved portion 12. Thus, when button 22*a* is depressed by the user curved portion 12 vibrates. Button 22*b* is operably coupled to a switch that controls flow to the means for imparting arcuate motion to the distal tip 16. Thus, when the button is depressed by the user the distal tip moves in an arcuate manner. Button 22*c* is operably coupled to a switch that selectively controls currently flow to both the means for imparting the vibratory effect to the curved portion 12 and the means for imparting arcuate motion to the distal tip 16. Thus, when button 22*c* is depressed the curved portion 12 vibrates and the distal tip 16 moves in an arcuate manner. Button 22*d* is operably coupled to a switch that controls the flow of current to the means for imparting the vibratory effect to the clitoral stimulation cup portion 18. Thus, when button 22*d* is depressed the clitoral stimulation cup portion 18. Multiple buttons may be depressed by the user to combine effects. For example button 22*a* and button 22*d* may be simultaneously depressed to provide simultaneous vibration of the curved portion 12 and vibration of the clitoral stimulation cup portion 18.

The above disclosure of the present invention has been provided in an illustrative sense and is not intended to be limiting. Numerous different embodiments and variations of the present invention may be made within the scope of the inventive concept disclosed herein.

I claim:

1. A sexual aid device, comprising:

a curved portion for insertion into a vagina or an anus, said curved portion having a proximal and a distal end;

a substantially straight portion, said straight portion extending from said proximal end of said curved portion thereby forming an approximate J shape; and mechanical means for causing both a vibrating motion of said curved portion and a movement of said distal end from one position to another position while said curved portion remains curved.

2. The device of claim 1 wherein said movement is arcuate.

3. The device of claim 1 wherein said movement is circular.

4. The device of claim 1 wherein said movement is an extending movement.

5. The device of claim 1 wherein said movement is a back-and-forth movement.

6. The device of claim 1 wherein said distal end of said curved portion stimulates a female's Grafenberg spot or G spot when the device is inserted into the vagina with said straight portion pointing away from said curved portion towards the female's torso.

7. The device of claim 1 wherein said straight portion extends coextensively from said curved portion.

8. The device of claim 1 and further comprising a clitoral stimulation portion.

9. The device of claim 8 wherein said clitoral stimulation portion is a cup.

10. The device of claim 9 wherein said clitoral stimulation portion is textured.

11. The device of claim 9 wherein said clitoral stimulation portion vibrates.

12. The device of claim 8 wherein said substantially straight portion includes a cover having a plurality of buttons; said plurality of buttons coupled to said mechanical means and for imparting vibratory motion to said curved portion, back-and-forth motion to said curved portion and vibratory motion to said clitoral stimulation portion.

13. The device of claim 1 further comprising a means for selectively employing only said vibrating motion or only said movement of said distal end or a combination of both.

* * * * *